US012622884B2

(12) United States Patent
Sánchez-Puelles González-Carvajal et al.

(10) Patent No.: US 12,622,884 B2
(45) Date of Patent: May 12, 2026

(54) TREATMENT AND PREVENTION OF GLIOBLASTOMA

(71) Applicants: CONSEJO SUPERIOR DE INVESTIGACIONES CIENTÍFICAS, Madrid (ES); ALIANZA ESPAÑOLA DE FAMILIAS DE VON HIPPEL-LINDAU-VHL, Olías del Rey (ES); CONSORCIO CENTRO DE INVESTIGACIÓN BIOMÉDICA EN RED, M.P., Madrid (ES)

(72) Inventors: José María Sánchez-Puelles González-Carvajal, Madrid (ES); Luisa María Botella Cubells, Madrid (ES); Tania Aguado Sanchez, Madrid (ES); Ángel Cuesta Martínez, Madrid (ES); Virginia Albiñana Díaz, Madrid (ES); Karina Villar Gomez-De Las Heras, Olías del Rey (ES)

(73) Assignees: CONSEJO SUPERIOR DE INVESTIGACIONES CIENTÍFICAS, Madrid (ES); ALIANZA ESPAÑOLA DE FAMILIAS DE VON HIPPEL-LINDAU-VHL, Olías del Rey (ES); CONSORCIO CENTRO DE INVESTIGACIÓN BIOMÉDICA EN RED, M.P., Madrid (ES)

( * ) Notice: Subject to any disclaimer, the term of this patent is extended or adjusted under 35 U.S.C. 154(b) by 1113 days.

(21) Appl. No.: 17/413,500

(22) PCT Filed: Dec. 12, 2019

(86) PCT No.: PCT/EP2019/084822

§ 371 (c)(1),
(2) Date: Jun. 11, 2021

(87) PCT Pub. No.: WO2020/120656

PCT Pub. Date: Jun. 18, 2020

(65) Prior Publication Data

US 2022/0008362 A1 Jan. 13, 2022

(30) Foreign Application Priority Data

Dec. 12, 2018 (EP) .................................... 18382917

(51) Int. Cl.
*A61K 31/138* (2006.01)
*A61K 45/06* (2006.01)

(52) U.S. Cl.
CPC ............ *A61K 31/138* (2013.01); *A61K 45/06* (2013.01)

(58) Field of Classification Search
CPC .............................. A61K 31/138; A61K 45/06
See application file for complete search history.

(56) References Cited

U.S. PATENT DOCUMENTS 11,730,707 B2 8/2023 Botella Cubells et al.

FOREIGN PATENT DOCUMENTS

| | | | |
|---|---|---|---|
| CN | 112804996 | 3/2020 | |
| CN | 115715804 | 3/2020 | |
| WO | WO2015/121500 * | 8/2015 | ............ A61K 31/00 |

OTHER PUBLICATIONS

Bernier M et al. Antitumor activity of (R,R')-4-methoxy-1-naphthylfenoterol in a rat C6 glioma xenograft model in the mouse. Pharmacol Res Perspect. Dec. 2013;1(2):e00010. doi: 10.1002/prp2.10. Epub Dec. 5, 2013. PMID: 2550 (Year: 2013).*
Zalcman N, Canello T, Ovadia H, Charbit H, Zelikovitch B, Mordechai A, Fellig Y, Rabani S, Shahar T, Lossos A, Lavon I. Androgen receptor: a potential therapeutic target for glioblastoma. Oncotarget. Apr. 13, 2018;9(28):19980-19993. doi: 10.18632/oncotarget.25007. PMID: 29731997; PMCID: PMC5929440. (Year: 2018).*
Beta Adrenergic Blocking Agents—LiverTox—NCBI Bookshelf 2018 (Year: 2018).*
Merriam-Webster Dictionary, Prevent, 2024, https://www.merriam-webster.com/dictionary/prevent (Year: 2024).*
Office action dated Feb. 4, 2024 in SIPO application No. 202280035018.8.
Shiro Komba, et al., Fucoxanthin Derivatives: Synthesis and their Chemical Properties, J. Oleo Sci., 2015; 64 (9): 1009-18 (doi: 10.5650/jos.ess15039. Epub Aug. 6, 2015.).
Therese A. Dolecek et al., "CBTRUS Statistical Report: Primary Brain and Central Nervous System Tumors Diagnosed in the United States in 2005-2009," Neuro-Oncology, Nov. 2012, 14 (Suppl 5):v1-v49.
Stella R. O'Donnell et al., "The importance of choice of agonist in studies designed to predict beta 2 : beta 1 adrenoceptor selectivity of antagonists from pA2 values on guinea-pig trachea and atria," Naunyn-Schmiedeberg's Arch. Pharmacol, Sep. 1979, pp. 183-190, vol. 308.
James A. Nathanson, "beta-adrenergic-Sensitive Adenylate Cyclase in Secretory Cells of Choroid Plexus," Science, May 25, 1979, pp. 843-844, vol. 204.
James A. Nathanson, "Cerebral Microvessels Contain a beta-2-Adrenergic Receptor," Life Sciences, Mar. 1980, pp. 1,793-1,799, vol. 26.
Kenneth P. Minneman et al., "The Pharmacological Specificity of Beta-1 and Beta-2 Adrenergic Receptors in Rat Heart and Lung in Vitro," Molecular Pharmacology, Jul. 1979, pp. 21-23, vol. 16.
Kenneth P. Minneman et al., "Comparison of Beta Adrenergic Receptor Subtypes in Mammalian Tissues," The Journal of Pharmacology and Experimental Therapeutics, Aug. 1979, pp. 502-508, vol. 211, No. 3.

(Continued)

*Primary Examiner* — Bruck Kifle
*Assistant Examiner* — Kevin S Martin
(74) *Attorney, Agent, or Firm* — Pilloff Passino & Cosenza LLP; Rachel Pilloff; Sean Passino

(57) ABSTRACT

The invention relates to the use of a selective $\beta_2$ adrenergic receptor antagonist for treating glioma. In particular, the invention relates to the use of an alkanolamine derivative or a pharmaceutically acceptable acid-addition salt thereof for treating a glioblastoma in a patient.

15 Claims, 7 Drawing Sheets

(56) References Cited

OTHER PUBLICATIONS

Figure 1:
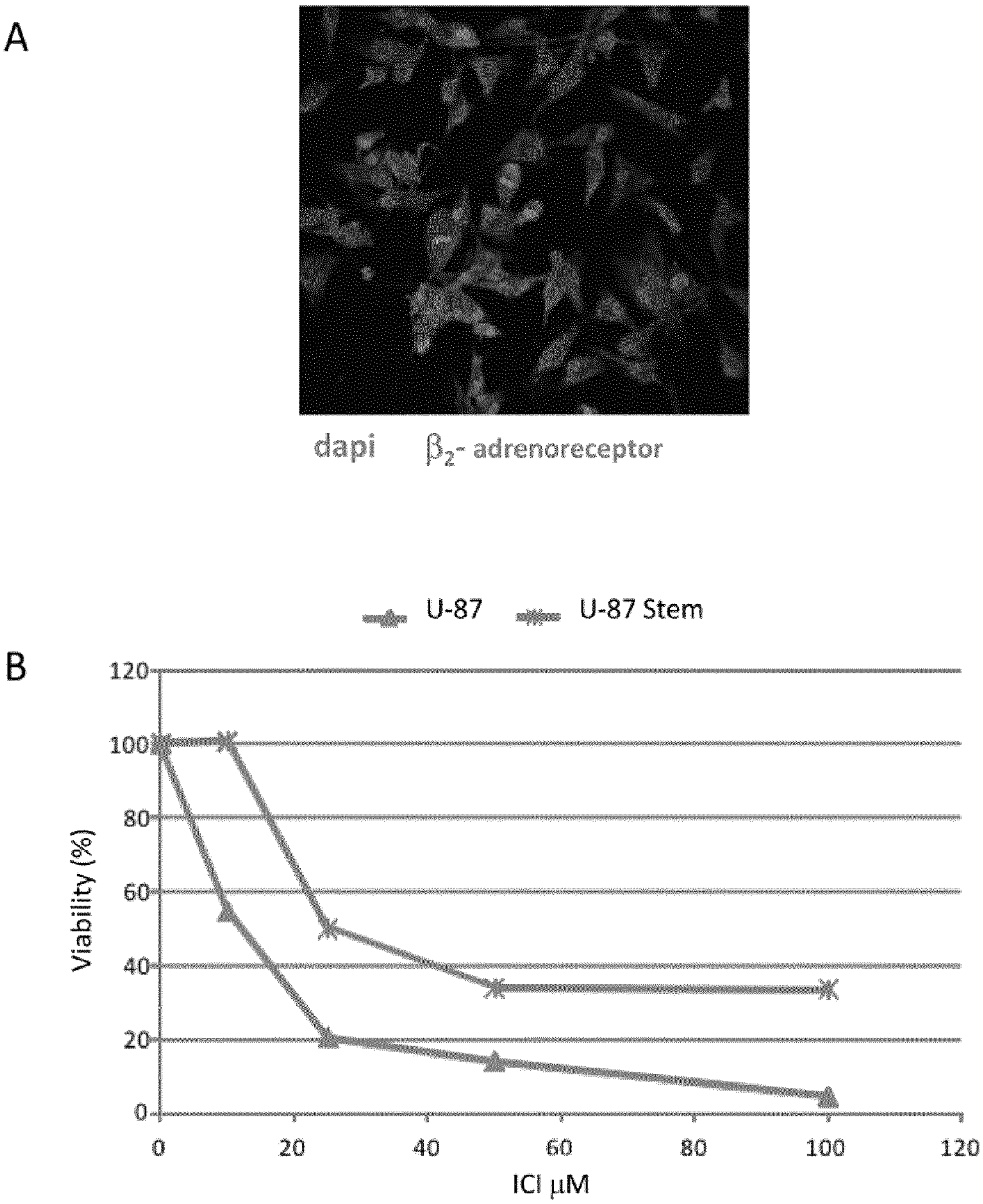
Figure 1:
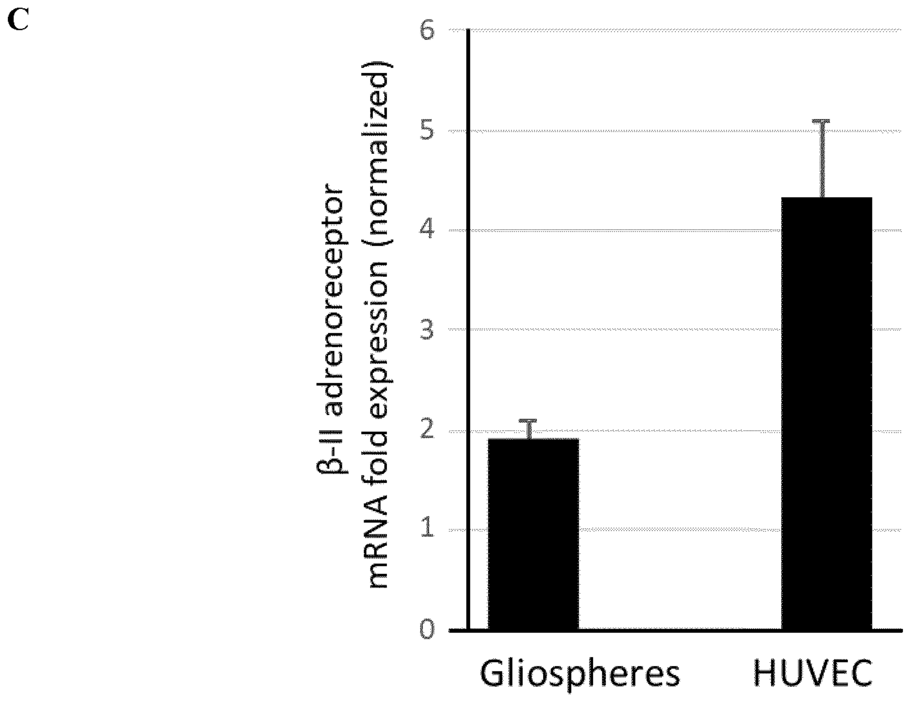

Stella R. O'Donnell et al., "Evidence That ICI 118, 551 Is a Potent, Highly Beta2-Selective Adrenoceptorantagonist and Can Be Used to Characterize Beta-Adrenoceptor Populations in Tissues," Life Sciences, Jun. 1989, pp. 671-677, vol. 27.

Andrew J. Bilski et al., "The Pharmacology of a beta-2-Selective Adrenoceptor Antagonist (ICI 118,551)," Journal of Cardiovascular Pharmacology, Jul. 1982, pp. 430-437, vol. 5.

U. Johansson et al., "On the stereospecificity of the beta-2-adrenoceptor blocking properties of prenalterol," J. Pharm. Pharmacol., Mar. 1980, pp. 659-660, vol. 32.

Shannon Reagan-Shaw et al., "Dose translation from animal to human studies revisited," The FASEB Journal, Mar. 2007, pp. 659-661, vol. 22.

Eva Diaz-Guerra et al., "Intrinsic cues and hormones control mouse mammary epithelial tree size," The FASEB Journal, May 2012, pp. 3,844-3,853, vol. 26.

Dario Ponti et al., "Isolation and In vitro Propagation of Tumorigenic Breast Cancer Cells with Stem/Progenitor Cell Properties," Cancer Research, Jul. 1, 2005, pp. 5,506-5,511, vol. 65, No. 13.

Yifang Hu, "ELDA: Extreme limiting dilution analysis for comparing depleted and enriched populations in stem cell and other assays," Journal of Immunological Methods, Jun. 2009, pp. 70-78, vol. 347.

Piyush B. Gupta et al., "Identification of selective inhibitors of cancer stem cells by high-throughput screening," Cell, Aug. 21, 2009, pp. 645-659, vol. 138, No. 4.

Tracy Seymour et al., "Targeting aggressive cancer stem cells in glioblastoma," Frontiers in Oncology, Jul. 2015, vol. 5.

Silvia Peñuelas et al., "TGF-beta Increases Glioma-Initiating Cell Self-Renewal through the Induction of LIF in Human Glioblastoma," Cancer Cell, Apr. 2009, pp. 315-327, vol. 15.

Jeongwu Lee et al., "Tumor stem cells derived from glioblastomas cultured in bFGF and EGF more closely mirror the phenotype and genotype of primary tumors than do serum-cultured cell lines," Cancer Cell, May 2006, pp. 391-403, vol. 9.

Lisa B. Frankel et al., "Programmed Cell Death 4 (PDCD4) Is an Important Functional Target of the MicroRNA miR-21 in Breast Cancer Cells," The Journal of Biological Chemistry, Jan. 11, 2008, pp. 1026-1033, vol. 283, No. 2.

Qian Zhou et al., "MicroRNAs as potential biomarkers for the diagnosis of glioma: A systematic review and meta- analysis," Cancer Science, Jun. 2018, pp. 2,651-2,659, vol. 109.

Kaijun Di et al., "Marizomib activity as a single agent in malignant gliomas: ability to cross the blood-brain barrier," Neuro-Oncology, Dec. 2016, pp. 840-848, vol. 18, No. 6.

Anonymous, "ICI 118551 hydrochloride, beta2 adrenoreceptor antagonist ab120808", Internet, Nov. 9, 2012 (Nov. 9, 2012), Retrieved from the Internet: URL:https ://www.abcam.com/ici-118551-hydrochloride-beta-2-adrenoreceptorantagonistab120808.html#top-O [retrieved on May 6, 2019].

Özlem Darcansoy Işeri et al, beta-Adrenoreceptor antagonists reduce cancer cell proliferation, invasion, and migration, Pharmaceutical Biology, Jul. 2014, pp. 1,374-1,381, vol. 52, No. 11.

F. Sarialioglu et al., "Propranolol in Tumors Except Infantile Hemangiomas: Presentation of Four Cases," Pediatric Blood and Cancer, Oct. 2014.

Ping Wang et al., "Expression of Beta-Adrenergic Receptor in Glioma LN229 Cells and Its Effect on Cell Proliferation," Advances in Computer Science Research, Jan. 2016, pp. 730-734, vol. 59, 7th International Conference on Education, Management, Computer and Medicine (EMCM 2016).

Pan Pantziarka, "Repurposing Drugs in Oncology (ReDO)-Propranolol as an anti-cancer agent," Dec. 2016, Ecancermedicalscience, vol. 10.

International Search Report & Written Opinion for PCT/EP2019/084822, mailed Mar. 12, 2020.

Borhane Annabi et al., "Propranolol adrenergic blockade inhibits human brain endothelial cells tubulogenesis and matrix metalloproteinase-9 secretion," Pharmacological Research, vol. 60, Issue 5, pp. 438-445 (Nov. 2009).

First Office Action dated Jun. 26, 2024 in SIPO application No. 01980091073.7.

L Toll, et al., {Beta}2-adrenergic receptor agonists inhibit the proliferation of 1321N1 astrocytoma cells, J Pharmacol Exp Ther, Feb. 2011; vol. 336, No. 2, pp. 524-532. doi: 10.1124/jpet.110.173971.

* cited by examiner

B

ICI

C

Propanolol

A

B

TREATMENT AND PREVENTION OF GLIOBLASTOMA

TECHNICAL FIELD OF THE INVENTION

The invention relates to the field of therapeutics and prevention of glioma, more specifically to the treatment and prevention of glioblastoma.

BACKGROUND OF THE INVENTION

A glioma is a type of cancer that starts in the brain or spine. It is called a glioma because it arises from glial cells and/or its precursors. The most common site of gliomas is the brain. Gliomas are classified by cell type, grade, and location. Gliomas are named according to the specific type of cell they most closely resemble. The main types of gliomas are:

- Ependymomas, gliomas derived from ependymal cells.
- Astrocytomas, gliomas derived from astrocytes; the glioblastoma multiforme (GBM) is the most common astrocytoma.
- Oligodendrogliomas, gliomas derived from oligodendrocytes.
- Mixed gliomas, such as oligoastrocytomas, that contain cells from different types of glia.

Gliomas are further categorized according to their grade, which is determined by pathologic evaluation of the tumor. Thus, it can be distinguished between low-grade gliomas that are well-differentiated (not anaplastic), benign and portend a better prognosis for the patient; and high-grade gliomas, that are undifferentiated or anaplastic, malignant and carry a worse prognosis.

Of numerous grading systems in use, the most common is the World Health Organization (WHO) grading system for astrocytoma.

The treatment for brain gliomas depends on the location, the cell type and the grade of malignancy. Often, treatment is a combined approach, using surgery, radiation therapy, and chemotherapy. The radiation therapy is in the form of external beam radiation or the stereotactic approach using radiosurgery. Spinal cord tumors can be treated by surgery and radiation. Temozolomide is a chemotherapeutic drug that is able to cross the blood-brain barrier effectively and is being used in therapy. Despite these approaches most high-grade glioma patients succumb to their disease. New therapeutic interventions to critical targets are needed to improve outcome in this patient population.

The glioblastoma multiforme (GBM, WHO grade IV) is a highly aggressive brain tumor presenting as one of two subtypes with distinct clinical histories and molecular profiles. The primary GBM presents acutely as a high-grade disease and the secondary GBM subtype evolves from the slow progression of a low-grade disease (Dolecek T A et al. 2012. Neuro Oncol 14 (Suppl 5):v1-v49.

Malignant gliomas, such as GBM, are by far the most common brain cancer found in adults and one of the most difficult to treat. Even with aggressive single and multimodal treatment options such as surgery, chemotherapy, radiation and small molecule inhibitors, the survival has remained unchanged over the past three decades with a median survival of less than one year after diagnosis. Reasons for the failure of conventional treatments is multifactorial including the highly infiltrative/invasive nature of GBM, limitation of drug delivery through the blood brain barrier and neural parenchyma, and genetic heterogeneity resulting in intrinsic resistance to available treatments and the rise of aggressive resistant clones. Therefore, there is a requirement for new treatment options.

BRIEF DESCRIPTION OF THE INVENTION

Figure 2:
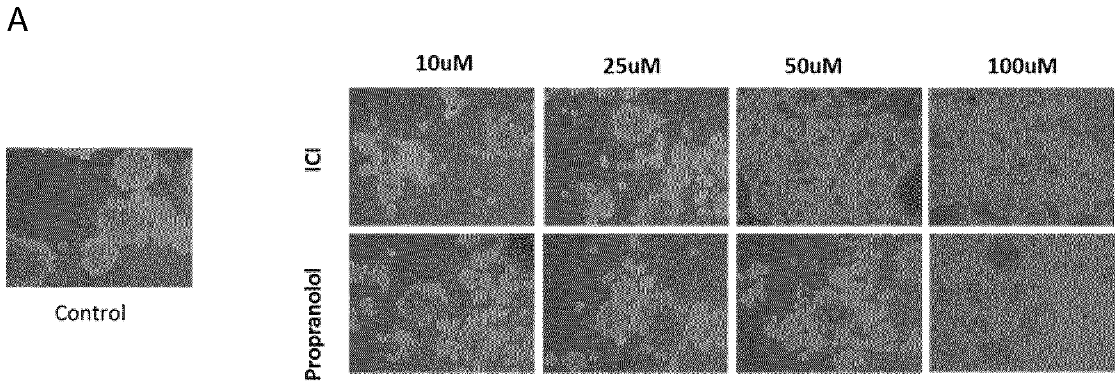
Figure 2:
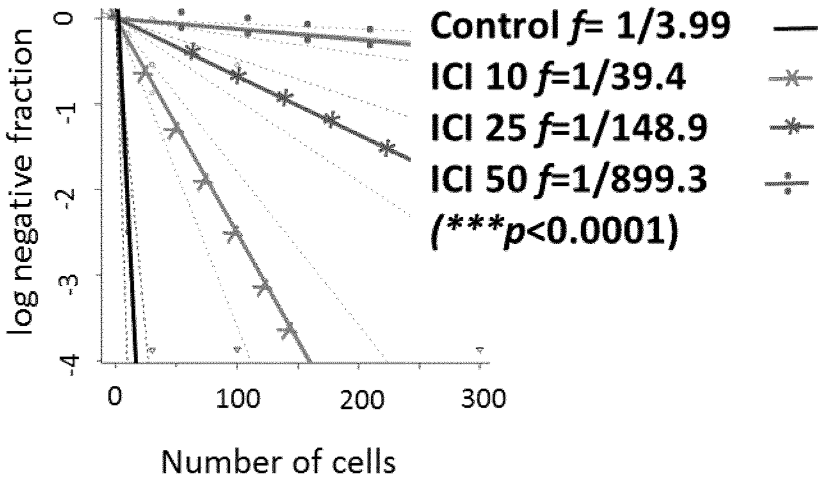
Figure 2:
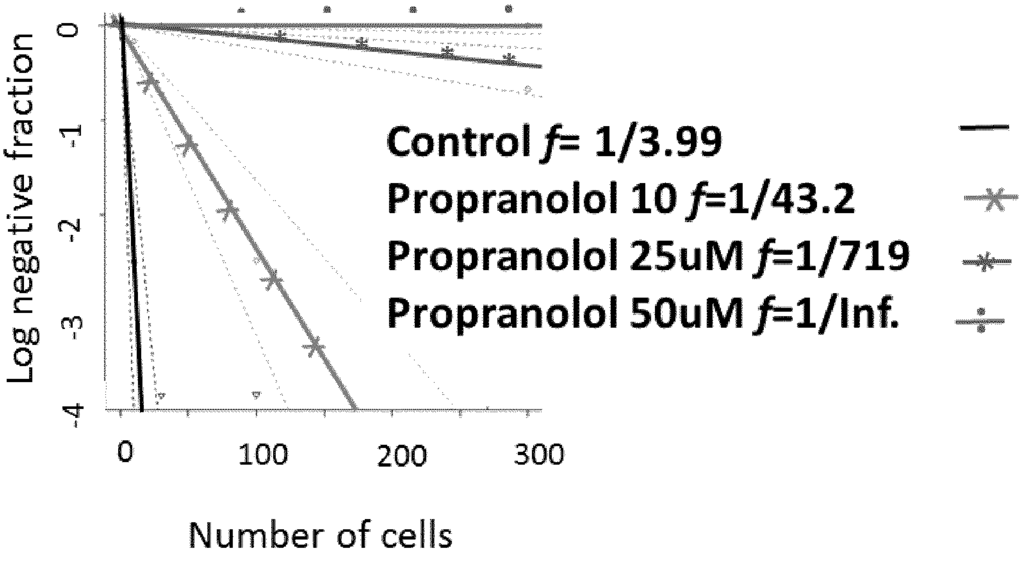

The inventors of the present invention have found that ICI 118,551 decreases viability of the glioblastoma cell line U-87 (FIG. 1) and inhibits formation and expansion of gliospheres, under the accepted culturing procedures for the subpopulation of cancer stem cells, from human glioblastoma (FIG. 2). Additionally, the inventors have shown that ICI 118,551 decreases stemness biomarker expression in glioblastoma, and increases neural differentiation markers (FIG. 3) and delays tumor progression in a mice xenograft model (FIG. 4).

Thus, the invention relates to a selective antagonist of the $\beta_2$-adrenergic receptor for use in the treatment and/or prevention of glioma.

DETAILED DESCRIPTION OF THE FIGURES

FIG. 1.—ICI 118,551 is active as an antitumoral agent decreasing cell viability in the glioblastoma cell line and including the stem cell subpopulation. A: U-87 cell line expresses beta-adrenergic receptors type 2, as shown by confocal microscopy using a monoclonal antibody against human $\beta_2$ adrenergic receptors (Abcam). B: ICI-118551 decreases viability of the human glioblastoma cell line U-87 either when grown in liquid suspension as oncospheres (gliospheres, stem cells) or in adhesion. Viability was quantified by luminescence using the ATP-Glo kit from Promega. C. $\beta_2$-adrenergic receptor expression in the human glioblastoma cell line U87 was confirmed by mRNA expression by quantitative PCR in 3D cultures as gliospheres (HUVEC as positive control for β2-adrenergic receptor expression).

FIG. 2.—ICI 118,551 inhibits the formation and expansion of gliospheres from the human glioblastoma cell line U-87. A: photographs of gliospheres formation after 72 hours of drug treatment. U-87 cells were cultured in medium for gliosphere formation, and either treated with vehicle (control, on the left), or with ICI 118,551, and propranolol at different concentrations from 10 to 100 μM. When cells were treated with beta blockers there is a progressive inhibition on the gliospheres formation, which is patent from 10 μM onwards. B: Limit dilution assay experiment (ELDA) for oncosphere formation in the presence of different concentrations of ICI 118,551 and propranolol. From the diagrams, it is clear that the dilution factor increases after treatment with ICI118,551 and with Propranolol, compared to control. This may very well be a consequence of stem cell sensitivity of U-87 stem cells to ICI 118,551 and to propranolol.

Figure 3:
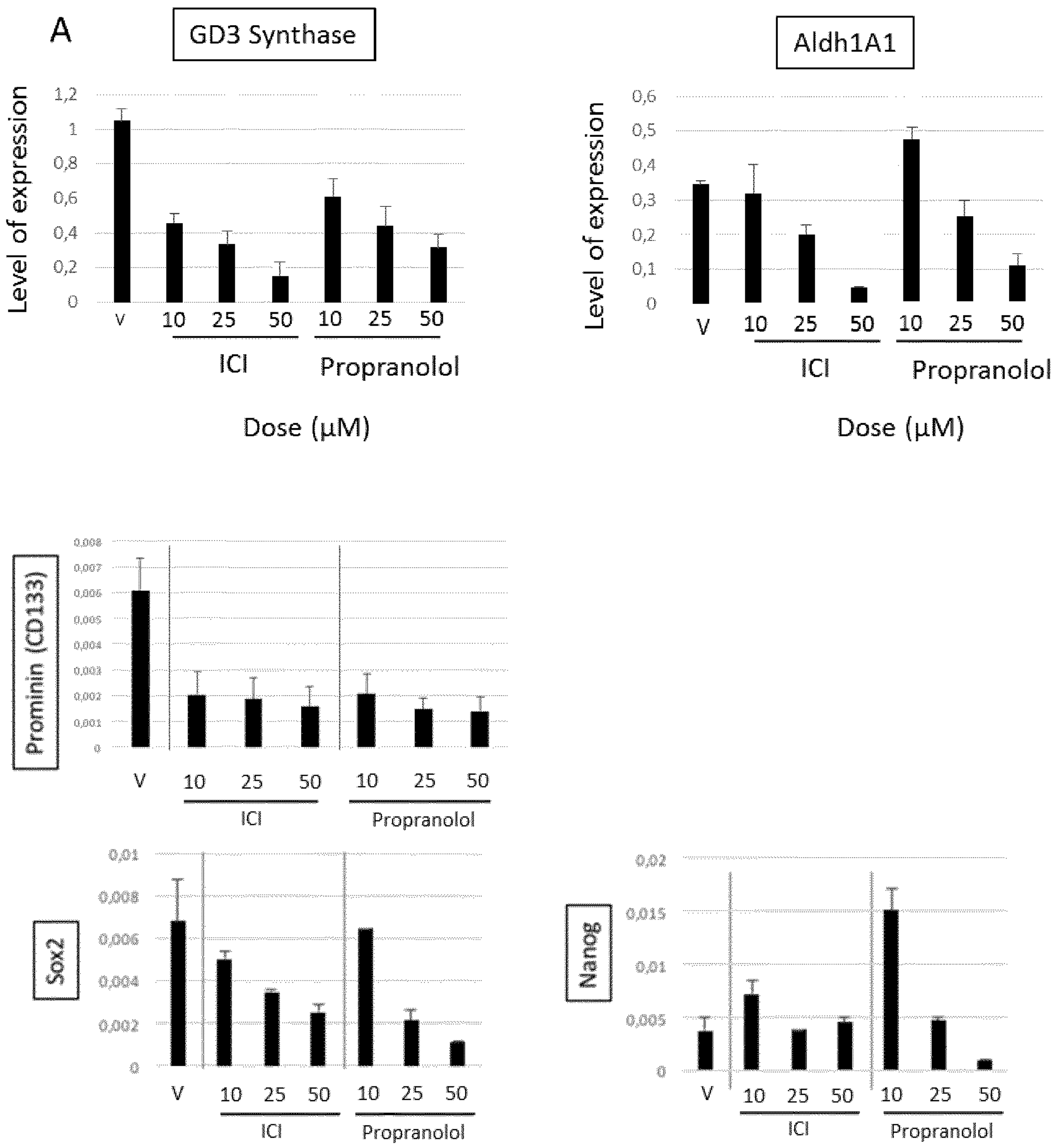
Figure 3:
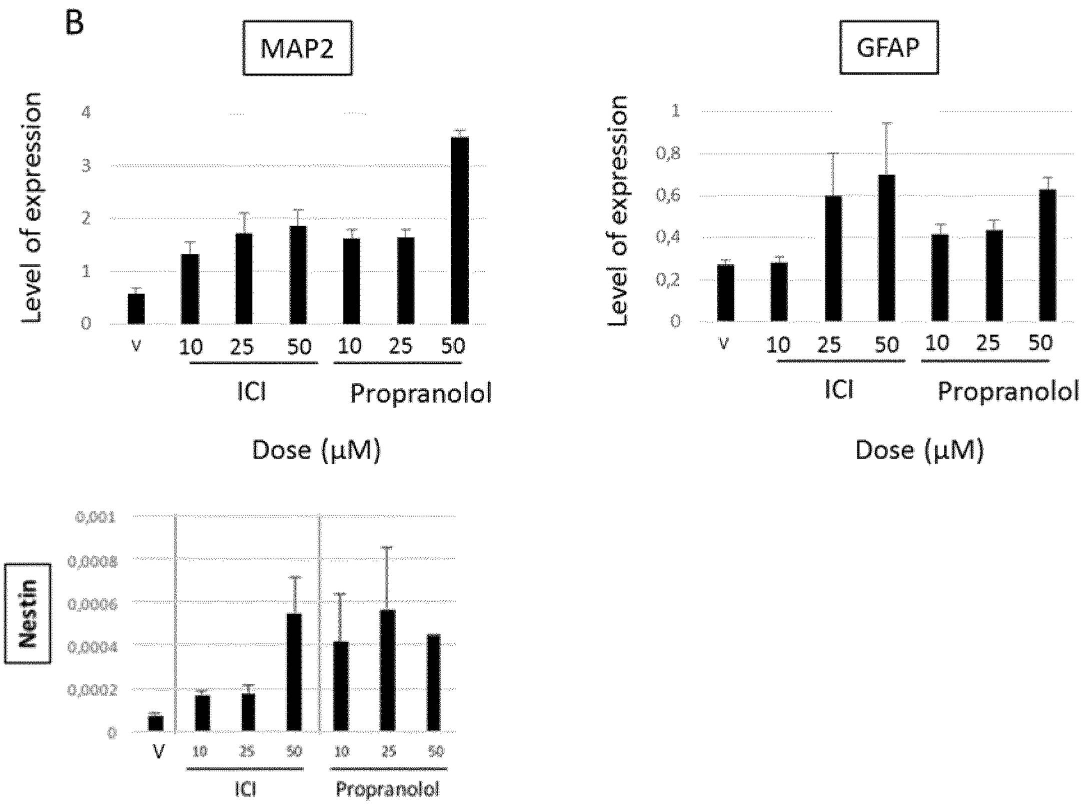
Figure 4:
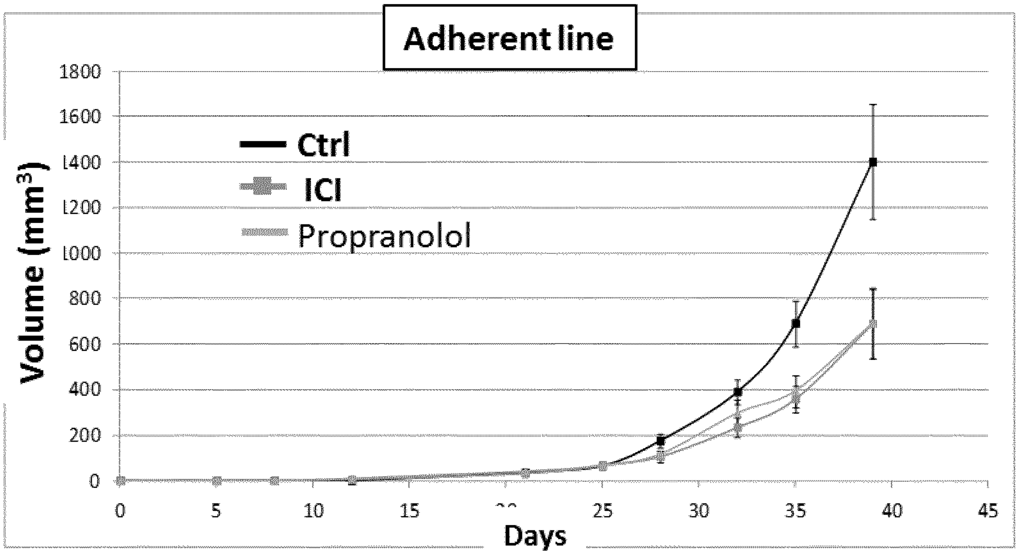
Figure 4:
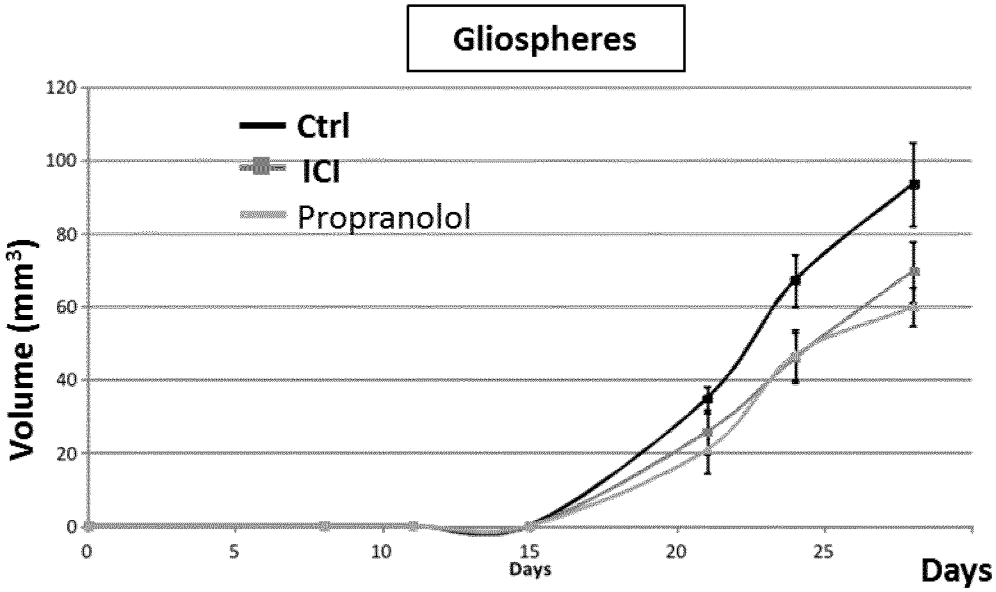

FIG. 3.—ICI 118,551 and propranolol decreased stemness biomarker expression in U-87 glioblastoma cell line, but increased the neural differentiation markers. A: The treatment of U-87 with ICI-118,551 and propranolol during 48 hours decreases the expression of stemness associated genes as GD3 synthase, ALDH1, Prominin (CD133), Sox2 and Nanog, whereas B: favors the expression of genes involved in neural cell differentiation (MAP2, GFAP and Nestin). Expression of the corresponding mRNAs was measured by RT-qPCR.

FIG. 4.—ICI 118,551 and Propranolol delay the tumor progression of U-87 xenografts in NSG immunodeppressed mice. A Xenograft using U-87 adherent cells: Mice (n=30) were inoculated with $10^6$ cells of U-87 glioblastoma cell line, in the flank, as xenografts. Tumor volume was measured every 3 days. In A, when tumors reached around 100 $mm^3$ volume, mice were divided in 3 groups (n=9-10). One group was treated daily with 10 mg/Kg body weight with propranolol, another group with the same dose of ICI118,551, and the third group only with vehicle (DMSO). Drugs were intraperitoneally injected. There were no adverse effects observed. B Xenograft using U-87 gliospheres: Mice were inoculated with $10^5$ spheroids from the glioblastoma cell line U-87. Mice were divided in 3 groups of 9-10 animals and treated immediately after xenograft for 5 consecutive days with either 3 mg/Kg body weight of propranolol, or ICI 118,551, or only vehicle. The tumors were measured from the moment they were big enough to be sized.

Figure 5:
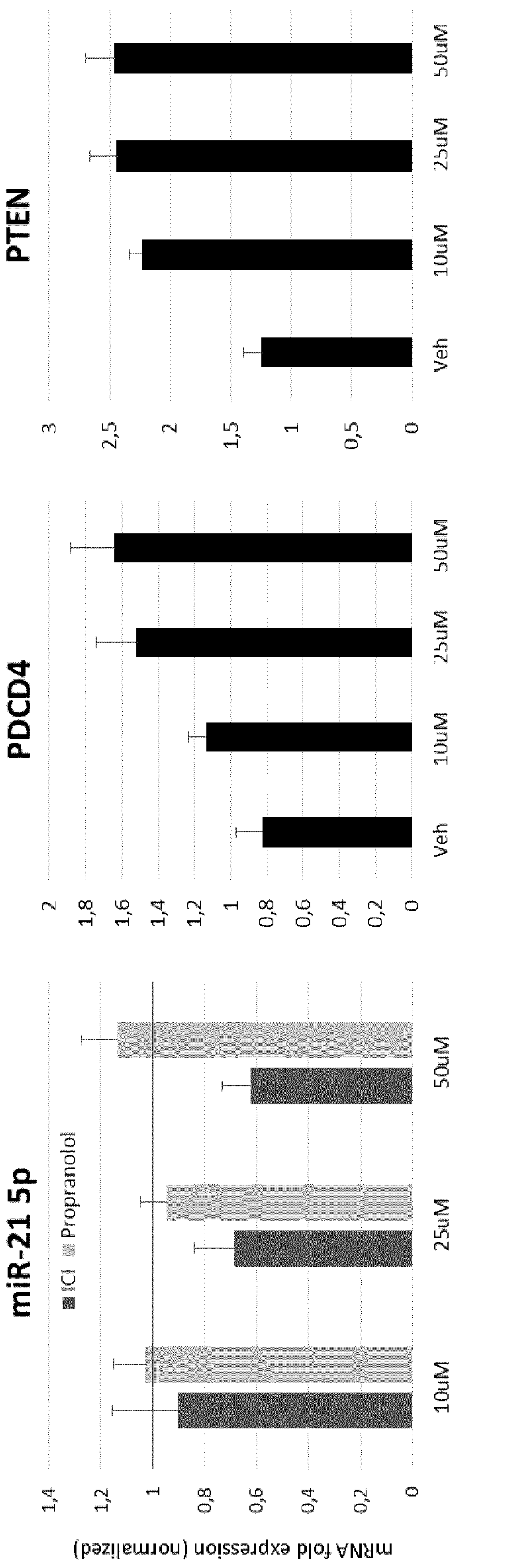

FIG. 5. U87 cells were cultured in DMEM-10% FCS and incubated for 48 hours with increasing amounts of ICI and Propranolol for 48 hours. mRNA-21 expression notably decreases after incubation with ICI when compared with Propranolol (left). Furthermore, ICI increases the expression levels of mRNA-21 targets such as PDCD4-proapoptotic agents1 (middle)—and PTEN—a glioblastoma suppressor (right).

DETAILED DESCRIPTION OF THE INVENTION

The invention relates to a selective antagonist of the $\beta_2$-adrenergic receptor for use in the treatment and/or prevention of glioma.

Alternatively, the invention relates to the use of a selective antagonist of the $\beta_2$-adrenergic receptor in the manufacture of a medicament for the treatment and/or prevention of glioma.

Alternatively, the invention relates to a method of treatment and/or prevention of glioma in a patient comprising administering to said patient a therapeutically effective amount of a selective antagonist of the $\beta_2$-adrenergic receptor.

The term "$\beta_2$-adrenergic receptor" or "β2AR", as used herein, refers to a class A of G protein-coupled receptors (GPCR) that responds to diffusible hormones and neurotransmitters and resides predominantly in smooth muscles. There are two main groups of adrenergic receptors, α and β, with several subtypes:

- α receptors have the subtypes $\alpha_1$ (a $G_q$ coupled receptor) and $\alpha_2$ (a $G_i$ coupled receptor).
- β receptors have the subtypes $\beta_1$, $\beta_2$ and $\beta_3$. All three are linked to $G_s$ proteins, which in turn are linked to adenylate cyclase. Agonist binding to these receptors causes a rise in the intracellular concentration of the second messenger cAMP.

Agonist binding to the $\beta_2$-adrenergic receptor results in smooth muscle relaxation.

The term "$\beta_2$-adrenergic receptor antagonist", as used herein, refers to a compound that binds a $\beta_2$-adrenergic receptor and lacks any substantial ability to activate the receptor itself. The term "$\beta_2$-adrenergic receptor antagonist" includes both neutral antagonists and inverse agonists. A "neutral antagonist" is a compound that blocks the action of the agonist but has no effect on intrinsic or spontaneous receptor activity. An "inverse agonist" is able to both block the action of the agonist at the receptor and attenuate the constitutive activity of the receptor. The term "antagonist" also includes competitive antagonists, which are drugs that bind to the same site as the natural ligand; noncompetitive antagonists which bind to a different site on the receptor than the natural ligand; reversible antagonists which bind and unbind the receptor at rates determined by receptor-ligand kinetics; and irreversible antagonists which bind permanently to the receptor either by forming a covalent bond to the active site or just by binding so tightly that the rate of dissociation is effectively zero.

The term "selective "$\beta_2$-adrenergic receptor antagonist", as used herein, means an antagonist which is selective for $\beta_2$-adrenergic receptors over $\beta_1$-adrenergic receptors. In a particular embodiment, a selective $\beta_2$-adrenergic receptor antagonist exhibits at least 10-fold greater potency in binding to $\beta_2$- than to $\beta_1$-adrenergic receptors, i.e. have a $\beta_2/\beta_1$ selectivity ratio of at least 10. More preferably, the selective $\beta_2$ receptor antagonist will have a $\beta_2/\beta_1$ selectivity ratio of at least 50. Still more preferably, the selective $\beta_2$ receptor antagonist will have a $\beta_2/\beta_1$ selectivity ratio of at least 123. The affinity of various active agents for $\beta_2$- and $\beta_1$-adrenergic receptors can be determined by evaluating tissues and/or cell subtypes containing a majority of $\beta_2$ receptors (e.g., rabbit ciliary process, rat liver, cat choroid plexus or lung), tissues containing a majority of $\beta_1$ receptors (e.g., cat and guinea pig heart), and tissues containing a mixture (e.g. guinea pig trachea). The methods of determining relative binding selectivity for these different types of tissues are extensively disclosed in O'Donnell and Wanstall, Naunyn-Schmiedeberg's Arch.Pharmaco., 308, 183-190 (1979), Nathanson, Science. 204, 843-844 (1979), Nathanson, Life Sciences, 26, 1793-1799 (1980), Minneman et al., Mol.Pharmacol., 15, 21-33 (1979a), and Minneman et al., Journal of Pharmacology and Experimental Therapeutics, 211, 502-508 (1979).

A significant number of compounds having selective $\beta_2$-adrenergic antagonist activity suitable for use in this invention are known. In a particular embodiment, the selective $\beta_2$-adrenergic receptor antagonist is the alkanolamine derivative of formula I Formula I

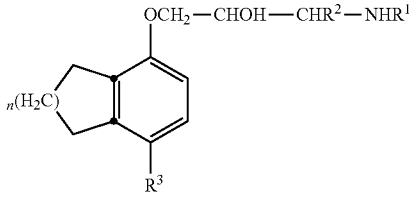

- wherein $R^1$ is an alkyl group of up to 6 carbon atoms which is branched at the α-carbon atom,
- wherein $R^2$ is an alkyl of up to 3 carbon atoms,
- wherein $R^3$ is hydrogen, an halogen or an alkyl of up to three carbon atoms and
- wherein n is 1 or 2,
- or a pharmaceutically acceptable acid addition salt thereof.

The term "alkyl group", as used herein, refers to acyclic straight and branched groups derivable from alkanes, and having the formula —CnH2n+1 by removal of a hydrogen atom.

The term "halogen", as used herein, refers to an atom selected from fluorine, chlorine, bromine and iodine.

$R^1$ may be, for example, isopropyl or t-butyl. In a particular embodiment, $R^1$ is isopropyl.

$R^2$ may be, for example, methyl or ethyl. In a particular embodiment, $R^2$ is methyl.

$R^3$ may be, for example, hydrogen, chlorine, bromine, methyl or ethyl. In a particular embodiment, $R^3$ is methyl.

In a particular embodiment n is 1.

In a particular embodiment, $R^1$ is isopropyl and $R^2$ is methyl. In a particular embodiment, $R^1$ is isopropyl and $R^3$ is methyl. In a particular embodiment, $R^1$ is isopropyl and n is 1. In a particular embodiment, $R^2$ is methyl and $R^3$ is methyl. In a particular embodiment, $R^2$ is methyl and n is 1. In a particular embodiment, $R^3$ is methyl and n is 1.

In a particular embodiment, $R^1$ is isopropyl and $R^2$ and $R^3$ are methyl. In another particular embodiment, $R^1$ is isopropyl, $R^2$ is methyl and n is 1. In another particular embodiment, $R^1$ is isopropyl, $R^3$ is methyl and n is 1. In a particular embodiment, $R^2$ and $R^3$ are methyl and n is 1.

In a more particular embodiment, $R^1$ is isopropyl, $R^2$ and/or $R^3$ are methyl and n is 1.

In an even more particular embodiment, the alkanolamine derivative has the formula II:

Formula II

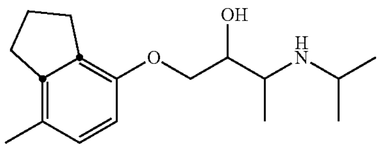

This compound of formula II is also known as ICI 118,551 and its chemical name is erythro-D,L-1(methylinden-4-yloxy)-3-isopropylaminobutan-2-ol. ICI 118,551 has a $\beta_2/\beta_1$ selectivity ratio of at least 123, as determined and reported in Life Sciences, 27,671 (1980) and Bilski et al., J. Cardiovasc.Pharmacol., 5, 430-437 (1983).

It will be observed that the alkanolamine derivative of formula I possesses two asymmetric carbon atoms, namely those of the —CHOH— group and the —CHR2- group, and that it can therefore exist in two racemic diastereoisomeric forms, the threo and erythro forms, and four optically-active forms, those being the (+) and (−) isomers of each of the racemic forms. It is to be understood that this invention encompasses any one of these isomeric forms which possess a selective $\beta_2$-adrenergic receptor antagonistic activity as defined above, it being a matter of common general knowledge how any particular isomer may be isolated and how any selective $\beta_2$-adrenergic receptor blocking activity it may possess may be measured.

It is to be understood that in general an optical isomer which has the {S)-absolute configuration of the —CHOH— group is more active as a $\beta_2$ adrenergic blocking agent than the corresponding isomer which has the {R)-absolute configuration. It is also known that in general the erythro-isomer is more $\beta_2$-selective than the corresponding threo-isomer, but that both threo-and erythro isomers of the compounds of the present invention possess the required selectivity.

The term "pharmaceutically acceptable acid-addition salt" refers to any acid-addition salt, which, upon administration to the recipient is capable of providing (directly or indirectly) a compound as described herein. Preferably, as used herein, the term "pharmaceutically acceptable salt" means approved by a regulatory agency of the Federal or a state government or listed in the U.S. Pharmacopeia or other generally recognized pharmacopeia for use in animals, and more particularly in humans. The preparation of salts can be carried out by methods known in the art. Illustrative non-limitative examples of pharmaceutically-acceptable acid-addition salt of the alkanolamine derivative of formula I is, for example, a salt derived from an inorganic acid, for example a hydrochloride, hydrobromide, phosphate or sulphate, or a salt derived from an organic acid, for example an oxalate, lactate, tartrate, acetate, salicylate, citrate, benzoate, β-naphthoate, adipate or 1,1-methylene-bis(2-hydroxy-3-naphthoate), or a salt derived from an acidic synthetic resin, for example a sulphonated polystyrene resin. In a particular embodiment, the pharmaceutically acceptable acid-addition salt is hydrochloride. In a more particular embodiment, the selective antagonist of the $\beta_2$ adrenergic receptor antagonist is the hydrochloride salt of the compound of formula II.

In another particular embodiment, the selective $\beta_2$-adrenergic receptor antagonist is selected from a list comprising the following compounds:

Butoxamine, corresponding to a compound having the chemical name DL-erythro-α-(2,5-dimethoxyphenyl)-β-t-butyl aminopropanol hydrochloride. Determination of the $\beta_2$ selectivity of butoxamine is reported in O'Donnell and Wanstall, Naunyn-Schmiedeberg's Arch.Pharmaco., 308, 183-190 (1979), which reports a $\beta_2/\beta_1$ selectivity ratio of at least 17.

H35/25, corresponding to 1-(4'-methylphenyl)-b 2,2-1-isopropylaminopropanol.

Prenalterol, having the structural formula

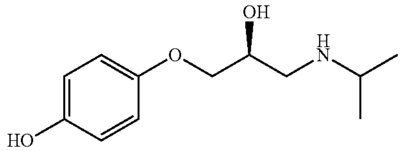 [SMILES: CC(C)NC[C@H](O)COc1ccc(O)cc1]

The selective $\beta_2$-adrenergic receptor antagonistic activity is described by Johansson and Waldeck, J. Pharm. Pharmacol., 1988, 32(9), 659-660.

Various 4- and 5-[2-hydroxy-3-(isopropylamino) propoxy]benzimidazoles as described by Crooks et al, J. Med. Chem., 22(2), 210-214 (1979).

1-(t-butyl-amino-3-ol-2-propyl)oximino-9 fluorene, as described by Imbs et al, Br. J. Pharmacol. 60(3), 357-362(1977).

Various 2-(alpha-hydroxyarylmethyl)-3,3-dimethylaziridines as described by Jain et al, J. Med. Chem., 21(1), 68-72 (1978).

The term "treatment", as used herein, refers to any process, action, application, therapy, or the like, wherein a subject (or patient), including a human being, is provided medical aid with the object of improving the subject's condition, directly or indirectly, or slowing the progression of a condition or disorder in the subject, or ameliorating at least one symptom of the disease or disorder under treatment.

The term "prevention", as used herein, refers to the administration of a compound of the invention in an initial or early stage of the disease, or to also prevent its onset.

The term "glioma", as used herein, is a common type of tumor originating in the brain. Gliomas originate in the glial cells that surround and support neurons in the brain, including astrocytes, oligodendrocytes and ependymal cells. Gliomas can be classified according to the specific type of cell with which they share histological features, but not necessarily from which they originate. The main types of gliomas are:

Ependymomas: ependymal cells.

Astrocytomas: astrocytes (glioblastoma multiforme is a malignant astrocytoma and the most common primary brain tumor among adults).

Oligodendrogliomas: oligodendrocytes.

Brainstem glioma: develop in the brain stem.

Optic nerve glioma: develop in or around the optic nerve.

Mixed gliomas, such as oligoastrocytomas, contain cells from different types of glia.

The term "glioma", as used herein, encompass all types of gliomas, including ependymomas, astrocytomas, oligodendrogliomas, brainstem glioma, optic nerve glioma and oligoastrocytomas. In a particular embodiment the glioma comprises a subpopulation of cancer stem cells. As disclosed herein, Cancer Stem Cells (CSCs) are a small subpopulation of cells within tumors with capabilities of self-renewal, differentiation, and tumorigenicity. It is known in the art that different biomarkers may be used to identify CSC, such as CD-44, Gremlin1, Id-1, TGFb2, BMP, OLIG2, SOX-2, ZEB1, Wnt5a, Pax-6, miRNSA-451, GD3S, ALDH1.

In a particular embodiment, the glioma is an astrocytoma. The term "astrocytoma" includes astrocytomas of grade I, II, III and IV, according to the WHO Classification of Tumors of the Central Nervous System. In a more particular embodiment, the astrocytoma is grade IV astrocytoma, also known as "glioma" or "glioblastoma multiforme".

Gliomas can also be further categorized according to their grade, which is determined by pathologic evaluation of the tumor. The neuropathological evaluation and diagnostics of brain tumor specimens is performed according to WHO Classification of Tumors of the Central Nervous System. According to their grade, they can be classified as:

Low-grade gliomas [WHO grade II] are well-differentiated (not anaplastic); these tend to exhibit benign tendencies and portend a better prognosis for the patient.

High-grade [WHO grades III-IV] gliomas are undifferentiated or anaplastic; these are malignant and carry a worse prognosis.

In a particular embodiment, the glioma is a high-grade glioma.

The glioma can be a primary tumor, or a recurrent tumor. The term "primary" or "non-recurrent", as used herein, refers to a tumor that appears for the first time in a subject, that is, a tumor that has not previously been detected and treated. The term "recurrent", as used herein, refers to a tumor that has appeared after a free-disease period, after treatment and after a period of time during which cancer was not detected. In a particular embodiment, the glioma is a primary or non-recurrent glioma.

In a preferred embodiment, the glioma is characterized by having increased expression of the $\beta_2$-adrenergic receptor compared to a reference value.

"Reference value", as used herein relates to a laboratory value used as a reference for the values/data obtained from samples. The reference value (or reference level) can be an absolute value, a relative value, a value which has an upper and/or lower limit, a series of values, an average value, a median, a mean value, or a value expressed by reference to a control or reference value. A reference value can be based on the value obtained from an individual sample, such as, for example, a value obtained from a sample of study but obtained at a previous point in time. The reference value can be based on a high number of samples, such as the values obtained in a population of samples or based on a pool of samples including or excluding the sample to be tested. In a particular embodiment, the reference value is the expression of the $\beta_2$-adrenergic receptor in a healthy subject. In another particular embodiment, the reference value is the expression of the $\beta_2$-adrenergic receptor in a subject not suffering from glioma.

The increase in the expression of the $\beta_2$-adrenergic receptor can be of at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100% with respect to a reference value.

Methods suitable for determining the expression of the $\beta_2$-adrenergic receptor include, without limitation, standard assays for determining mRNA expression levels such as qPCR, RT-PCR, RNA protection analysis, Northern blot, RNA dot blot, in situ hybridization, microarray technology, tag based methods such as serial analysis of gene expression (SAGE) including variants such as LongSAGE and SuperSAGE, microarrays, fluorescence in situ hybridization (FISH), including variants such as Flow-FISH, qFISH and double fusion FISH (D-FISH), and the like.

The term "patient" or "subject", as used herein, refers to any animal, preferably a mammal and includes, but is not limited to, domestic and farm animals, primates and humans, for example, human beings, non-human primates, cows, horses, pigs, sheep, goats, dogs, cats, or rodents. In a preferred embodiment, the subject is a human being of any age or race. In the present invention, the patient suffers from a glioma, more particularly from astrocytoma, even more particularly from glioblastoma.

The term "patient with glioma", as used herein, means that the patient has been diagnosed with glioma. Diagnosis of glioma may involve:

A medical history and physical exam, which includes questions about the patient's symptoms, personal and family health history.

A neurological exam: This exam tests vision, hearing, speech, strength, sensation, balance, coordination, reflexes and the ability to think and remember. It may also include an examination on patient's eyes to look for any swelling caused by pressure on the optic nerve, which connects the eyes to the brain.

Scans of the brain: Magnetic resonance imaging (MRI) and computed tomography (CT or CAT scan), which use computers to create detailed images of the brain, are the most common scans used to diagnose brain tumors.

A biopsy: This is a procedure to remove a small sample of the tumor for examination under a microscope. Depending on the location of the tumor, the biopsy and removal of the tumor may be performed at the same time.

For its administration to the patient, the selective $\beta_2$ adrenergic receptor antagonist of the invention, preferably the alkanolamine derivative of formula I, more preferably the alkanolamine derivative of formula II, or a pharmaceutically acceptable acid-addition salt thereof, can be formulated in a pharmaceutical composition.

The term "pharmaceutical composition", as used herein, refers to a composition comprising a therapeutically effective amount of the selective $\beta_2$ adrenergic receptor antagonist of the invention, preferably the alkanolamine derivative of formula I, more preferably the alkanolamine derivative of formula II, or a pharmaceutically acceptable acid-addition salt thereof, and at least a pharmaceutically acceptable excipient or carrier.

The term "therapeutically effective amount", as used herein, refers to the sufficient amount of the compound to provide the desired effect and will generally be determined by, among other causes, the characteristics of the compound itself and the therapeutic effect to be achieved. It will also depend on the subject to be treated, the severity of the disease suffered by said subject, the chosen dosage form, administration route, etc. For this reason, the doses mentioned in this invention must be considered only as guides for the person skilled in the art, who must adjust the doses depending on the aforementioned variables.

Even though individual needs vary, determination of optimal ranges for therapeutically effective amounts of the compounds for use according to the invention belongs to the common experience of those experts in the art. In general, the dosage needed to provide an effective treatment, which can be adjusted by one expert in the art, will vary depending on age, health, fitness, sex, diet, weight, degree of alteration of the receptor, frequency of treatment, nature and condition of the injury, nature and extent of impairment or illness, medical condition of the subject, route of administration, pharmacological considerations such as activity, efficacy, pharmacokinetic and toxicology profile of the particular compound used, if using a system drug delivery, and if the compound is administered as part of a combination of drugs. The amount of the compound for use according to the invention that is therapeutically effective in the prevention and/or treatment of ischemia/reperfusion injury in a subject can be determined by conventional clinical techniques (see, for example, The Physician's Desk Reference, Medical Economics Company, Inc., Oradell, NJ, 1995, and Drug Facts and Comparisons, Inc., St. Louis, MO, 1993).

In a particular embodiment, the therapeutically effective amount produces the amelioration of one or more symptoms of glioma. In a particular embodiment, the selective $\beta_2$ adrenergic receptor antagonist, preferably the alkanolamine derivative of formula I, more preferably the alkanolamine derivative of formula II, or the pharmaceutically acceptable acid-addition salt thereof, is administered at a dose from about 0.2 mg/kg/day to about 5 mg/kg/day, preferably from about 0.5 mg/kg/day, about 0.7 mg/kg/day, about 1 mg/kg/day, about 1.5 mg/kg/day about 1.7 mg/kg/day, about 1.9 mg/kg/day, about 2.1 mg/kg/day, about 2.2 mg/kg/day, about 2.5 mg/kg/day, about 2.7 mg/kg/day, about 2.9 mg/kg/day, to about 4.9 mg/kg/day, about 4.7 mg/kg/day, about 4.5 mg/kg/day about 4.3 mg/kg/day, about 4.1 mg/kg/day, about 3.9 mg/kg/day, about 3.7 mg/kg/day about 3.5 mg/kg/day, about 3.3 mg/kg/day, 3.1 mg/kg/day, about 3 mg/kg/day. In a more particular embodiment, the selective $\beta_2$ adrenergic receptor antagonist, preferably the alkanolamine derivative of formula I, more preferably the alkanolamine derivative of formula II, or the pharmaceutically acceptable acid-addition salt thereof, is administered at a dose between 2 mg/kg body/day and 3 mg/kg body/day. In an even more particular embodiment, the selective $\beta_2$ adrenergic receptor antagonist, preferably the alkanolamine derivative of formula I, more preferably the alkanolamine derivative of formula II, or the pharmaceutically acceptable acid-addition salt thereof, is administered at a dose of 2.4 mg/kg body/day.

Doses of the compounds of the invention may be expressed either in mg of the antagonist per kg of body weight or in mg of the antagonist per square meter of body surface. The skilled person knows how to determine the dose for a particular animal, in particular the dose for human beings, from the doses experimentally assayed in mice. For example, the article from Reagan-Shaw S. et al. (Reagan-Shaw S. et al. "*Dose translation from animal to human studies revisited*". FASEB J 2008, 22(3):659-661) provides the standard conversion factors used to convert mg/kg to mg/m$^2$.

$$\text{Dose (mg/kg)} \times K_m = \text{Dose (mg/m}^2\text{)}$$

The article also explains that this conversion is the basis for converting dose in a first animal species to dose in a second animal species (allometric dose translation). Thus, animal dose (AD) in mg/kg can be converted to human equivalent dose (HED) in mg/kg using the following formula:

$$HED\,(\text{mg/kg}) = AD\,(\text{mg/kg}) \times \frac{\text{Animal } K_m}{\text{Human } K_m}$$

wherein the $K_m$ for each species is shown in Table 1 (data extracted from Reagan-Shaw S. et al. "*Dose translation from animal to human studies revisited*". FASEB J 2008, 22(3): 659-661).

TABLE 1

| $K_m$ factor for conversion of AD to HED | | |
|---|---|---|
| Species | | $K_m$ factor |
| Human | Adult | 37 |
| | Child | 25 |
| Baboon | | 20 |
| Dog | | 20 |
| Monkey | | 12 |
| Rabbit | | 12 |
| Guinea pig | | 8 |
| Rat | | 6 |
| Hamster | | 5 |
| Mouse | | 3 |

Thus, the experiments with doses of 30 mg/kg in mice correspond to general doses in humans of 2.4 mg/kg.

In another particular embodiment, the selective $\beta_2$ adrenergic receptor antagonist, preferably the alkanolamine derivative of formula I, more preferably the alkanolamine derivative of formula II, or the pharmaceutically acceptable acid-addition salt thereof, is administered in humans, at a dose wherein each administration ranges from 0.2 mg/kg to 5 mg/kg. preferably from about 0.2 mg/kg/day, about 0.25 mg/kg/day, about 0.3 mg/kg/day, about 0.35 mg/kg/day, about 0.4 mg/kg/day, about 0.45 mg/kg/day, about 0.50 mg/kg/day, about 0.55 mg/kg/day, about 0.6 mg/kg/day, about 0.65 mg/kg/day, about 0.7 mg/kg/day, about 0.75 mg/kg/day, about 0.8 mg/kg/day, about 0.85 mg/kg/day, about 0.90 mg/kg/day, about 0.95 mg/kg/day, about 1 mg/kg/day, about 1.2 mg/kg/day, about 1.4 mg/kg/day, about 1.6 mg/kg/day, about 1.8 mg/kg/day, about 2 mg/kg/day about 2.2 mg/kg/day, about 2.4 mg/kg/day, about 2.6 mg/kg/day, about 2.8 mg/kg/day, about 3 mg/kg/day, about 3.2 mg/kg/day, to about 3.4 mg/kg/day, about 3.6 mg/kg/day, about 3.8 mg/kg/day, about 4 mg/kg/day, about 4.5 mg/kg/day, about 5 mg/kg/day. In a more preferred embodiment, the selective $\beta_2$ adrenergic receptor antagonist, preferably the alkanolamine derivative of formula I, more preferably the alkanolamine derivative of formula II, or the pharmaceutically acceptable acid-addition salt thereof, is administered at a dose between 2 mg/kg body/day and 3 mg/kg body/day. In a still more preferred embodiment, the selective $\beta_2$ adrenergic receptor antagonist, preferably the alkanolamine derivative of formula I, more preferably the alkanolamine derivative of formula II, or the pharmaceutically acceptable acid-addition salt thereof, is administered at a dose of 2.4 mg/kg body/day.

In another particular embodiment, the selective $\beta_2$ adrenergic receptor antagonist, preferably the alkanolamine derivative of formula I, more preferably the alkanolamine derivative of formula II, or the pharmaceutically acceptable acid-addition salt thereof, is administered daily preferably 1 time a day, 2 times a day, 3 times a day. In a more preferred embodiment, it is administered 1 time a day. In another particular embodiment, the selective $\beta_2$ adrenergic receptor antagonist, preferably the alkanolamine derivative of formula I, more preferably the alkanolamine derivative of formula II, or the pharmaceutically acceptable acid-addition salt thereof, is administered during 2 days, 3 days, 4 days, 5 days, 7 days, 9 days 10 days, 15 days, 20 days, 25 days, 1 month, 2 months, 3 months, 4 months, 5 months, 6 months, 7 months, 8 months, 9 months, 10 months, 11 months, 12 months or more than 12 months, preferably during 5 days, even more preferably during 5 consecutive days.

The terms "pharmaceutically acceptable excipient" or "pharmaceutically acceptable carrier", refer to any compound or combination of compounds that is essentially non-toxic to the subject at the dosage and concentration employed, and is compatible with the other components of a pharmaceutical composition. Thus, an excipient is an inactive substance formulated alongside the active ingredient (i.e., the selective $\beta_2$ adrenergic receptor antagonist, preferably the alkanolamine derivative of formula I, more preferably the alkanolamine derivative of formula II, or the pharmaceutically acceptable acid-addition salt thereof) of a pharmaceutical composition, for the purpose of bulking-up compositions that contain said active ingredients. Bulking up allows convenient and accurate dispensation of a drug substance when producing a dosage form. Excipients also can serve various therapeutic enhancing purposes, such as facilitating compound (drug) absorption or solubility, or other pharmacokinetic considerations. Excipients can also be useful in the manufacturing process, to aid in the handling of the active substance concerned such as by facilitating powder flowability or non-stick properties, in addition to aiding in vitro stability such as prevention of denaturation over the expected shelf life. The selection of appropriate excipients depends upon the rout of administration and the dosage form, as well as the active ingredient and other factors. An excipient can be a non-toxic solid, semisolid or liquid filler, diluent, encapsulating material or formulation auxiliary of any conventional type. Illustrative, non-limitative, examples of excipients or carriers include water, salt (saline) solutions, alcohol, dextrose, vegetable oils, polyethylene glycols, gelatin, lactose, amylose, magnesium stearate, talc, surfactants, silicic acid, viscous paraffin, perfume oil, monoglycerides and diglycerides of fatty acids, fatty acid esters petroetrals, hydroxymethyl cellulose, polyvinylpyrrolidone and the like.

The selective $\beta_2$ adrenergic receptor antagonist of the invention, preferably the alkanolamine derivative of formula I, more preferably the alkanolamine derivative of formula II, or a pharmaceutically acceptable acid-addition salt thereof, may be administered by any suitable administration route, such as, but not limited to, parenteral, oral, topical, nasal, rectal, intravitreal route. In a particular embodiment, the selective $\beta_2$ adrenergic receptor antagonist of the invention, preferably the alkanolamine derivative of formula I, more preferably the alkanolamine derivative of formula II, or a pharmaceutically acceptable acid-addition salt thereof, is administered intraperitoneally, intravenously, subcutaneously, intradermically, intramuscularly or intravitreal. In a preferred embodiment, the selective $\beta_2$ adrenergic receptor antagonist of the invention, preferably the alkanolamine derivative of formula I, more preferably the alkanolamine derivative of formula II, or pharmaceutically acceptable acid-addition salt thereof, is administered orally or intravenously or intravitreal. In a more preferred embodiment, the selective $\beta_2$ adrenergic receptor antagonist of the invention, preferably the alkanolamine derivative of formula I, more preferably the alkanolamine derivative of formula II, or pharmaceutically acceptable acid-addition salt thereof, is administered intraperitoneally.

In a preferred embodiment, the selective antagonist of the $\beta_2$-adrenergic receptor is administered together with an antitumor compound. The term "tumor" or "cancer", as used herein, refers to a broad group of diseases involving unregulated cell growth and which are also referred to as malignant neoplasms. The term is usually applied to a disease characterized by uncontrolled cell division (or by an increase of survival or apoptosis resistance) and by the ability of said cells to invade other neighboring tissues (invasion) and spread to other areas of the body where the cells are not normally located (metastasis) through the lymphatic and blood vessels, circulate through the bloodstream, and then invade normal tissues elsewhere in the body. In a particular embodiment, the cancer appears as a benign tumor, i.e. tumors that cannot spread by invasion or metastasis, i.e., they only grow locally. In another particular embodiment, the cancer appears as a malign tumor, i.e. a tumor that is capable of spreading by invasion and metastasis.

As used herein, the terms "antitumor agent", "anticancer agent" or "antineoplastic agent" (indistinctly used in this description), generally refers to substances which inhibit or suppress the growth and proliferation of cancer cells. Antitumor agents may also include compounds that destroy cancer cells or interfere with cell division, compounds that block certain hormones involved in cancer, compounds that inhibit or prevent the growth of new blood vessels (e.g. angiogenesis inhibitors), agents that damage DNA (e.g. alkylating agents, such as cisplatin, carboplatin, and oxaloplatin; anti-metabolites; and topoisomerase inhibitors), and compounds with anticancer properties (e.g., taxanes, vinca alkaloids, and plant alkaloids). The term "antitumor agent" also includes radiation therapy. An antitumor agent may also include an agent specific for deregulated proteins of cancer cells. In a preferred embodiment, the antitumor compound is selected from leptomycin B (LMB, CAS number 87081-35-4) temozolomide (CAS number 85622-93-1), capecitabine (CAS number 154361-50-9) and an alkylating, intercalating or DNA damaging agent. In a more preferred embodiment, the antitumor compound is propranolol (CAS number: 525-66-6).

As disclosed herein an "alkylating agent" is a compound that attaches an alkyl group to the guanine base of the DNA molecule, preventing the strands of the double helix from linking as they should and causing a breakage of the DNA strands, affecting the ability of the cancer cell to multiply.

As disclosed herein an "intercalating agent" is a compound that inserts itself into the DNA structure of a cell and binds to the DNA, causing DNA damage. In cancer treatment, DNA intercalating agents may kill cancer cells by damaging their DNA and stopping them from dividing.

As disclosed herein a "DNA damaging agent" is an agent that damages DNA by affecting the primary structure of the double helix; that is, the bases themselves are chemically modified. Non-limiting examples of damaging agents include: reactive oxygen species, ultraviolet radiation, x-rays and gamma rays.

The term "administered together with an antitumor compound" means that the selective antagonist of the $\beta_2$-adrenergic receptor can be administered simultaneously or sequentially with the antitumor compound. When the selective antagonist of the $\beta_2$-adrenergic receptor and the antitumor compound are administered simultaneously, they can be found in a single pharmaceutical composition, or in different pharmaceutical compositions. When the selective antagonist of the $\beta_2$-adrenergic receptor and the antitumor compound are administered sequentially, they can be administered in any order, that is, the administration of the selective antagonist of the $\beta_2$-adrenergic receptor can start before the administration of the antitumor compound or the administration of the antitumor compound can start before the administration of the selective antagonist of the $\beta_2$-adrenergic receptor.

In a preferred embodiment, the selective antagonist of the $\beta_2$-adrenergic receptor is administered after the first line of therapy to patients who are no longer susceptible of continuing the first line therapy due to a relapse of the disease or to too severe secondary effects. In a preferred embodiment, the selective antagonist of the $\beta_2$-adrenergic receptor is administered as a second line of therapy. As disclosed herein, "second line of therapy" refers to a treatment which is administered to patients who have previously received a first therapy, known as "first line of therapy". The first line of therapy is often part of a standard set of treatments, such as surgery followed by chemotherapy and radiation. Also called induction therapy, primary therapy, and primary treatment. As disclosed herein, any first line of therapy may be used. Non-limiting examples of first line of therapy for glioma include: maximal surgical resection, radiotherapy, either used individually or radiotherapy plus concomitant and maintenance treatment with temozolomide (TMZ). Other examples of first line therapy for glioma includes anticancer compounds as defined above such as agents that damage DNA such as alkylating agents (e.g. cisplatin, carboplatin, and oxaloplatin); anti-metabolites; topoisomerase inhibitors, other compounds with anticancer properties (e.g., taxanes, vinca alkaloids, and plant alkaloids). In a preferred embodiment, the antitumor compound is selected from leptomycin B (LMB, CAS number 87081-35-4) temozolomide (CAS number 85622-93-1), capecitabine (CAS number 154361-50-9) and an alkylating, intercalating or DNA damaging agent. In a more preferred embodiment, the antitumor compound is propranolol (CAS number: 525-66-6).

In a particular embodiment, the selective antagonist of the $\beta_2$-adrenergic receptor is administered as the first line of therapy, that is, as the first treatment for glioma.

In a preferred embodiment, the selective antagonist of the $\beta_2$-adrenergic receptor is administered during a disease-free period. The term "disease-free period", as used herein, refers to a period during and/or after treatment in which a patient is living with a disease that does not get worse. In a preferred embodiment, the selective antagonist of the $\beta_2$-adrenergic receptor is administered during the disease-free period occurring after the treatment with a first line of therapy, although the invention also contemplates that the administration of the selective antagonist of the $\beta_2$-adrenergic receptor is done during other disease-free periods which the patient may experience after different lines of therapy (after a second line or therapy, after a third line of therapy or further lines of therapy). In another embodiment, the selective antagonist of the $\beta_2$-adrenergic receptor is administered after the second line of therapy, after the third line of therapy or after any line of therapy once the patient is no longer susceptible of continuing the line therapy due to a relapse of the disease or to too severe secondary effects.

The invention will be described by way of the following examples which are to be considered as merely illustrative and not limitative of the scope of the invention.

EXAMPLES

Materials and Methods

Oncosphere Culture and Extreme Limited Dilution Assay (ELDA)

Following the protocol described elsewhere (Diaz-Guerra, E.; Lillo, M. A.; Santamaria, S.; Garcia-Sanz, J. A., Intrinsic cues and hormones control mouse mammary epithelial tree size. *FASEB J* 2012, 26 (9), 3844-53). Cells were detached from the plate with trypsin (Invitrogen) and plated in complete medium (DMEM/F-12 medium with GlutaMAX) supplemented with B27 (Gibco), 10 ng/ml epidermal growth factor (EGF: Invitrogen) and 10 ng/ml basic fibroblast growth factor (bFGF: Millipore) and they were maintained at 37° C. in 5% $CO_2$. For the ELDA assay cells were dissociated to single cells with trypsin, and seeded at different dilutions (from 100 to 10 for U-87 cells) in sphere complete media following procedures described in Ponti, D et al., (*Cancer Res* 2005, 65 (13), 5506-11.). The final number of spheres was quantified at 14 days, and the final data and statistical significance was obtained with ELDA software (Hu, Y. et al *J Immunol Methods* 2009, 347 (1-2), 70-8).

RNA Extraction and Relative Quantification of miRNA and mRNA $RNA_t$ was isolated using the Direct-zol RNA MiniPrep Kit (ZymoResearch) from U-87 cells washed with PBS, scraped off the plates and spun down. The pellet was treated with the Tri Reagent and homogenized for 5 min at room temperature before using the MiniPrep Kit as per instructions. The quality and concentration of the RNAt was evaluated by measuring the absorbance at 260, 230 and 280 nm with an ND-1000 spectrophotometer (NanoDrop Technologies, Wilmington, DE, USA). In all cases, the expected 260/280 (~2.0) and 260/230 (2.0-2.2) ratio values accepted for pure RNA were obtained. To detect the two target miRs, 0.5 μg of the $RNA_t$ extracted from the cells was used for hybridization prior to measurement on the dual amperometric platform.

The qScript microRNA Quantification System (Quanta BioSciences, Inc., Gaithersburg, MD, USA) was used to assess miR-21 and miR-205 expression. In brief, cDNA was synthesized using the qScript microRNA cDNA Synthesis Kit, using 10 ng of initial RNA per PCR reaction. The PCR conditions consisted of an initial activation at 50° C. for 2 min, followed by 40 cycles of 95° C. for 5 s, and 60° C. for 30 s in LightCycler 480 Real-Time PCR System (Roche). The $C_t$ (threshold cycle) value for each primer was normalized to that of RNU6. To assess gene expression, cDNA was synthesized with the transcriptor first strand cDNA synthesis Kit (Roche) under the following PCR conditions: 40 amplification cycles of 95° C. for 10 seconds, 60° C. for 30 seconds and 72° C. for 30 seconds. ACTB was used as a reference gene for normalization and the real-time PCR reactions were performed in triplicate using the PerfeCTa SYBR Green SuperMix (Quanta BioSciences) for miRNAs and the FastStart Universal SYBR Green Master (Roche) for gene expression. The expression level of each gene was determined by the relative standard curve method and the primer sequences for target genes were obtained from the Universal ProbeLibrary Assay Design Center.

Confocal Microscopy

Cells were plated and grown on coverslips in P-24 well plates, in DMEM containing 10% FBS. After growth, for at least 24 hours, cells were fixed in the coverslips for 1 hour at 4° C. in 3.5% PFA/PBS. Next cells were permeabilized with 0.2% Triton X-100 in PBS for 30 min at RT. After that, a monoclonal rabbit primary antibody against $\beta_2$ human adrenergic receptor (Abcam) was incubated at 1:50 dilution in PBS for 60 minutes, followed by 3 washes with PBS, and the incubation with Alexa-488 anti-rabbit secondary diluted 1:100 in PBS for 1 hour. Coverslips were mounted with Prolong Gold with 4,6-diamidino-2-phenylindole (Invitrogen) and observed with a spectral confocal microscope Leica TCS SP2 (Leica Microsystems, Inc., Wetzlar, Germany).

Xenografts of U-87 Glioblastoma Cells and Gliospheres

Male 7-8 weeks old NOD scid gamma (NSG) mice were injected in the dorsal flank with a total of either $10^6$ cells of U-87 cell line (A), or with $10^5$ cells coming from disaggregated gliospheres (B). In the case of A, when tumor size reached 100 $mm^3$ volume, mice were divided at random in 3 groups, of 9/10 mice each. One group was treated with intraperitoneal daily injection of 10 mg/Kg body of propranolol, other group with the same amount of ICI118,551, and finally, a control group was injected with vehicle. Tumor size was measured by a caliper every 2-3 days. Mice were sacrificed when tumor volume average of the control group reached an end point established on our ethical procedures.

In the case of B, mice were divided in 3 groups of 10 mice, and were treated the first 5 days after xenograft establishment with intraperitoneal injection of propranolol, or ICI118,551 at 3 mg/Kg body, or vehicle. Mice were followed until tumors appeared and were sizeable. From this moment on, tumor size was measured every 2-3 days along 4 weeks, and then the mice were sacrificed.

Statistical Analysis

The values presented are the means±SEM or ±SD and the data from two groups were compared with a t test using GraphPad Prism 5. One-way analysis of variance (ANOVA) was used to determine the differences of the means for multiple pair-wise comparisons, with $p<0.05$ considered significant.

Results

ICI 118,551 Decreases the Viability and Increases the Apoptosis of U-87 Cells (Human Glioblastoma) In Vitro Since ICI 118,551 is a selective $\beta_2$ blocker, first thing to test was the expression of beta-adrenergic receptors type 2 in U-87 cell line. As shown in FIG. 1A, the use of confocal microscopy with a monoclonal antibody against human $\beta_2$ adrenergic receptors (Abcam) demonstrates that U-87 express this type of adrenergic receptor (FIG. 1A, cells stained), thus enabling the drug to exert its mechanism of action in this cellular model of glioblastoma. $\beta_2$ adrenergic receptor mRNA expression was also confirmed by quantitative PCR in 3D cultures as gliosphere (FIG. 1C).

Once the mechanism of ICI 118,551 was corroborated in U-87, cells were treated at different doses and it was apparent that this drug decreased the viability of this human glioblastoma cell line model, quantified by luminescence using the ATP-Glo kit from Promega, either when grown in liquid suspension as oncospheres (gliospheres, stem cells) or in adhesion (FIG. 1B). From FIG. 1B the results show that ICI 118,551 decreases the viability of U-87 in a different way when compared the treated liquid culture of 3D gliospheres with the 2D U-87 cells grown in adhesion. Differential sensitivity to the drug is shown in FIG. 1B, being more sensitive the cells grown in adhesion than the 3D gliospheres formed in suspension. This last is a general behavior in most anti-cancer drugs but, what is relevant is that ICI 118,551 strongly affects the viability of the cancer stem cells at low μM concentrations, which is in the basis of the processes of metastasis and recurrence of the oncological disease.

ICI 118,551 Inhibits the Formation and Expansion of Gliospheres, the Well-Accepted Culturing Procedure for Cancer Stem Cells, in the Human Glioblastoma Cell Line U-87.

U-87 gliospheres were cultured under specific conditions described elsewhere (Gupta, P. B. et al. 2009. *Cell,* 138, 645; Seymour, T. et al. 2015. *Front. Oncol.* 5:159. doi:10.3389/fonc.2015. 00159; Peñuelas et al. 2009. *Cancer Cell* 15, 315-327; -Lee, J. et al. 2006. *Cancer Cell* 9, 391-403). As shown in FIG. 2A, U-87 formed rounded mature gliospheres showing well defined structures. U-87 cells were cultured in medium for gliosphere formation, and either treated with vehicle (control, on the left), ICI 118,551 and propranolol, at different concentrations from 10 to 100 μM. When cells were treated with beta blockers there was a dose-dependent inhibition on the gliospheres formation, which is patent from 10 μM onwards in both drugs, propranolol and ICI-118,551. B: Limit dilution assay experiment (ELDA) for oncosphere formation in the presence of different concentrations of ICI 118,551 and propranolol. From the diagrams, it is clear that the dilution factor increases after treatment with ICI-118,551 and with propranolol, compared to control. This is a consequence of stem cell sensitivity of U-87 stem cells to ICI 118,551 and to propranolol.

ICI 118,551 and Propranolol Decreased the mRNA Expression of Stemness Biomarkers Expression in U-87 Glioblastoma Cell Line.

When U-87 cells were treated with ICI-118,551 and propranolol during 48 hours, the expression of stemness associated genes GD3 synthase, ALDH1, prominin (CD 133), Sox2 and nanog decreased significantly (FIG. 3A). However, mRNA from genes involved in neural cell differentiation, such as MAP2, GFAP and nestin (FIG. 3B), were increased in their expression (FIG. 3B). The expression of the corresponding mRNAs was measured by RT-qPCR. Conclusion was that while the expression of the chosen biomarkers of stemness were decreasing those associated with cell differentiation were increasing, all of them in a dose-dependent manner, and overall suggesting a role of ICI-118,551 in cell fate.

ICI 118,551 and Propranolol Delay the Tumor Progression of U-87 Xenografts in NSG Immunodeppressed Mice.

Xenografts were made using U-87 adherent cells: Mice (n=30) were inoculated with $10^6$ cells of U-87 glioblastoma cell line, in the flank, as xenografts. Tumor volume was measured every 3 days. When tumors reached around 100 $mm^3$ volume, mice were divided in 3 groups (n=9-10). One group was treated daily with 10 mg/Kg body weight with propranolol, another group with the same dose of ICI118, 551, and the third group only with vehicle (DMSO). Drugs were intraperitoneally injected. There were no adverse effects observed. As shown in FIG. 4A, there was a significant decrease in the tumor volume, around 30%, in the groups of mice treated with 10 mg/Kg body either of propranolol or ICI118,551.

On the other hand, xenografts using U-87 gliospheres were also used. These gliospheres are enriched in CSC (Cancer Stem Cells). Mice were inoculated with $10^5$ spheroids from the glioblastoma cell line U-87. Mice were divided in 3 groups of 9-10 animals each, and treated immediately after xenograft for 5 consecutive days with either 3 mg/Kg body weight of propranolol, or ICI 118,551, or only vehicle. The tumors were measured from the moment they were big enough to be sized. As can be seen in FIG. 4B, there was a significant delay in the rate of tumor growth between treated mice versus the vehicle treated mice during the first 5 days.

ICI 118,551 Induces a Greater Reduction in the mRNA-21 Expression than Propranolol in U87 Glioblastoma Cell Line The mechanism underlying the effects of miR-21 on tumorigenesis remains unclear, not least because only a few targets for this miR have been experimentally verified. The oncomiR miR-21 is known to exert transcriptional control over PDCD4 in malignant cells and its endogenous protein is up-regulated 3.5-fold by miR-21 inhibition. PDCD4 expression is down-regulated or lost in several tumor types making it a promising molecular target for the treatment of some cancers (Frankel, L. B., et al., J Biol Chem, 2008. 283(2): p. 1026-33). The re-expression of miR-21 has been associated with the acquisition of epithelial-mesenchymal transition in breast cancer and glioblastoma (Zhou Q, Liu J, Quan J, Liu W, Tan H, Li W. Cancer Sci. 2018 September; 109(9):2651-2659).

U87 cells were cultured in DMEM-10% FCS and incubated for 48 hours with increasing amounts of ICI and Propranolol for 48 hours. mRNA-21 expression notably decreased after incubation with ICI when compared with Propranolol (FIG. 5 left). Furthermore, ICI increases the expression levels of mRNA-21 targets such as PDCD4-proapoptotic agents1 (middle)—and PTEN—a glioblastoma suppressor (right).

The invention claimed is:

1. A method of treatment of glioma in a patient comprising administering to said patient a therapeutically effective amount of a selective antagonist of the $\beta_2$-adrenergic receptor, wherein the selective antagonist of the $\beta_2$-adrenergic receptor is the compound of formula

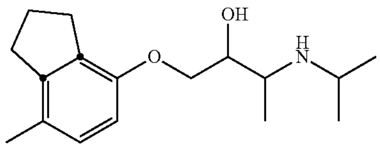

or a pharmaceutically acceptable acid addition salt thereof; and wherein the patient is a human patient.

2. The method according to claim 1, wherein the glioma is characterized by having increased expression of the $\beta_2$-adrenergic receptor compared to a reference value.

3. The method according to claim 1, wherein the antagonist is administered together with an antitumor compound selected from propanonol, temozolomide, leptomycin B and capecitabine.

4. The method according to claim 3, wherein the antitumor compound is propranolol.

5. The method according to claim 1, wherein the glioma comprises a subpopulation of cancer stem cells.

6. The method according to claim 1, wherein the glioma is a high-grade glioma.

7. The method according to claim 1, wherein the glioma is a non-recurrent glioma.

8. The method according to claim 1, wherein the glioma is astrocytoma.

9. The method according to claim 8, wherein the astrocytoma is glioblastoma.

10. The method according to claim 1, wherein the pharmaceutically acceptable acid-addition salt is hydrochloride.

11. The method according to claim 1, wherein the compound or pharmaceutically acceptable acid-addition salt thereof is administered at a dose between 1 mg/Kg body/day and 4.5 mg/kg body/day.

12. The method according to claim 11, wherein the alkanolamine derivative or pharmaceutically acceptable acid-addition salt thereof is administered at a dose between 2 mg/Kg body/day and 3 mg/kg body/day.

13. The method according to claim 12, wherein the alkanolamine derivative or pharmaceutically acceptable acid-addition salt thereof is administered at a dose of 2.4 mg/kg body/day.

14. The method according to claim 1, wherein the antagonist is administered to a patient as a first line of therapy or after a first line of therapy.

15. The method according to claim 1, wherein the selective antagonist of the beta-2 adrenergic receptor is therapeutically effective against glioma.

* * * * *